(12) United States Patent
Joseph et al.

(10) Patent No.: US 7,998,977 B2
(45) Date of Patent: Aug. 16, 2011

(54) INHIBITORS OF AKT (PROTEIN KINASE B)

(75) Inventors: Sajan Joseph, Indianapolis, IN (US);
Renhua Li, Fishers, IN (US); Michael Ray Myers, Fishers, IN (US); Aktham Aburub, Indianapolis, IN (US); Jenny Pingqi Dai, Hershey, PA (US); Christopher Randall Schmid, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 412 days.

(21) Appl. No.: 12/300,358

(22) PCT Filed: Jun. 12, 2007

(86) PCT No.: PCT/US2007/070945
§ 371 (c)(1),
(2), (4) Date: Nov. 11, 2008

(87) PCT Pub. No.: WO2007/149730
PCT Pub. Date: Dec. 27, 2007

(65) Prior Publication Data
US 2009/0221633 A1    Sep. 3, 2009

Related U.S. Application Data

(60) Provisional application No. 60/805,260, filed on Jun. 20, 2006, provisional application No. 60/885,765, filed on Jan. 19, 2007.

(51) Int. Cl.
*A01N 43/42* (2006.01)
*A61K 31/47* (2006.01)
*C07D 217/00* (2006.01)
(52) U.S. Cl. ...................................... 514/307; 546/139
(58) Field of Classification Search ................. 514/307; 546/139
See application file for complete search history.

(56) References Cited

FOREIGN PATENT DOCUMENTS

| WO | WO01/91754 | 12/2001 |
|---|---|---|
| WO | WO2004/094386 | 11/2004 |
| WO | WO2005/011697 | 2/2005 |
| WO | WO2005/054202 | 6/2005 |
| WO | WO 2005054202 A1 * | 6/2005 |

OTHER PUBLICATIONS

Reuveni, H., "Toward a PKB Inhibitor: Modification of a Selective PKA Inhibitor by Rational Design," Biochemistry, 2002, 41, pp. 10304-10314.

* cited by examiner

*Primary Examiner* — Sreeni Padmanabhan
*Assistant Examiner* — Samira Jean-Louis
(74) *Attorney, Agent, or Firm* — Tina M. Tucker; Danica Hostettler

(57) ABSTRACT

4-[5-(2-Amino-ethanesulfonyl)-isoquinolin-7-yl]-phenol or a pharmaceutically acceptable salt thereof or a hydrate of the compound or the salt thereof as Akt inhibitors that are antineoplastic and/or antiviral agents as well as compositions comprising these compounds and methods of using these compounds.

16 Claims, No Drawings

INHIBITORS OF AKT (PROTEIN KINASE B)

This is the national phase application, under 35 U.S.C. 371, for PCT/US2007/070945 filed Jun. 12, 2007, which claims the priority of U.S. Provisional Application Nos. 60/805,260, filed Jun. 20, 2006 and 60/885,765, filed Jan. 19, 2007.

The present invention provides compounds that are inhibitors of Akt, compositions comprising these compounds, and methods of using these compounds.

BACKGROUND OF THE INVENTION

Protein kinases are involved in the signal transduction pathways linking growth factors, hormones and other cell regulation molecules to cell growth, survival and metabolism under both normal and pathological conditions. One such protein kinase, protein kinase B (also known as Akt), is a serine/threonine kinase that plays a central role in promoting the proliferation and survival of a wide range of cell types, thereby protecting cells from apoptosis (programmed cell death).

A number of protein kinases and phosphatases regulate the activity of Akt. For instance, activation of Akt is mediated by phosphatidylinositol 3-kinase (PI3-K), which initiates the binding of second messenger phospholipids to the pleckstrin homology (PH) binding domain of Akt. The binding anchors Akt to plasma membrane and results in phosphorylation and activation of the enzyme. Amplifications of the catalytic subunit of PI3-K, p110α, or mutations in the PI3-K regulatory subunit, p85α, lead to activation of Akt in several types of human cancer. Recent studies have also demonstrated the role of the PI3-K/AKT pathway in the life cycle of numerous viruses.

WO 01/91754 pertains to protein kinase inhibitors. WO 2005/011697 involves protein kinase A and B inhibitors. WO 2005/054202 pertains to AKT inhibitors.

Because of its pivotal role in the regulation of cell survival, Akt provides a novel therapeutic target for the effective treatment of various disorders, particularly cancer and viral infections. However, such treatment requires the development of potent, selective, bioavailable inhibitors of Akt. A need exists for alternative Akt inhibitors. Thus, the present invention provides novel inhibitors of Akt that exhibit increased potency, selectivity, and/or bioavailability, compositions comprising these compounds, and methods of using these compounds.

Additionally, pharmaceutical compositions containing novel inhibitors of Akt when diluted or in solution necessarily must be free from precipitation in order to be delivered to a patient. The present invention provides pharmaceutical compositions comprising novel Akt inhibitors at particular pH ranges that lack such precipitation.

SUMMARY OF THE INVENTION

The present invention provides 4-[5-(2-amino-ethanesulfonyl)-isoquinolin-7-yl]-phenol or a pharmaceutically acceptable salt thereof or a hydrate of the compound or the salt thereof.

The present invention also provides 4-[5-(2-amino-ethanesulfonyl)-isoquinolin-7-yl]-phenol di-hydrochloride.

The present invention further provides 4-[5-(2-amino-ethanesulfonyl)-isoquinolin-7-yl]-phenol monohydrochloride hemihydrate.

The present invention also provides 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for use as a medicament.

Additionally, the present invention provides the use of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the manufacture of a medicament for treating multiple myeloma, non small cell lung cancer, glioblastoma, neuroblastoma, melanoma or neoplasms of the prostate, breast, ovaries, primary stomach, intestinal-type, endometrium, thyroid, pancreas, lung, or bladder.

The present invention also provides the use of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the manufacture of a medicament for treating multiple myeloma, non small cell lung cancer, glioblastoma or neoplasms of the prostate, breast, or ovaries.

The present invention additionally provides the use of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the manufacture of a medicament for treating non small cell lung cancer or glioblastoma.

The present invention further provides the use of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the manufacture of a medicament for treating hepatitis C, rubella, human immunodeficiency virus (HIV), hepatitis B, or human cytomegalovirus (HCMV).

Additionally, the present invention provides 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the treatment of multiple myeloma, non small cell lung cancer, glioblastoma, neuroblastoma, melanoma or neoplasms of the prostate, breast, ovaries, primary stomach, intestinal-type, endometrium, thyroid, pancreas, lung, or bladder.

The present invention also provides 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the treatment of multiple myeloma, non small cell lung cancer, glioblastoma or neoplasms of the prostate, breast, or ovaries.

The present invention additionally provides 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the treatment of non small cell lung cancer or glioblastoma.

The present invention further provides 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, for the treatment of hepatitis C, rubella, human immunodeficiency virus (HIV), hepatitis B, or human cytomegalovirus (HCMV).

The present invention additionally provides a method of treating multiple myeloma, non small cell lung cancer, glioblastoma, neuroblastoma, melanoma or neoplasms of the prostate, breast, ovaries, primary stomach, intestinal-type, endometrium, thyroid, pancreas, lung, or bladder in a patient in need thereof comprising administering an effective amount of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate.

The present invention also provides a method of treating multiple myeloma, non small cell lung cancer, glioblastoma or neoplasms of the prostate, breast, or ovaries in a patient in need thereof comprising administering an effective amount of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate.

The present invention additionally provides a method of treating non small cell lung cancer or glioblastoma in a patient in need thereof comprising administering an effective amount of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate.

The present invention further provides a method of treating hepatitis C, rubella, human immunodeficiency virus (HIV), hepatitis B, or human cytomegalovirus (HCMV) in a patient in need thereof comprising administering an effective amount of 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate.

The present invention also provides a pharmaceutical composition comprising 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, and a pharmaceutically acceptable carrier, diluent or excipient.

The present invention additionally provides a lyophilized pharmaceutical composition comprising 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, and a pharmaceutically acceptable carrier, diluent or excipient wherein the pH of said composition when diluted with aqueous diluent is less than 4.2 and greater than 2.0, less than 3.2 and greater than 2.0, or less than 2.8 and greater than 2.0.

The present invention also provides a pharmaceutical composition comprising 4-[5-(2-amino-ethanesulfonyl)-isoquinolin-7-yl]-phenol or a pharmaceutically acceptable salt thereof or a hydrate of the compound or the salt thereof, including 4-[5-(2-amino-ethanesulfonyl)-isoquinolin-7-yl]-phenol di-hydrochloride or 4-[5-(2-amino-ethanesulfonyl)-isoquinolin-7-yl]-phenol monohydrochloride hemihydrate, and a pharmaceutically acceptable carrier, diluent or excipient in solution wherein the pH of said composition is less than 4.2 and greater than 2.0, less than 3.2 and greater than 2.0, or less than 2.8 and greater than 2.0.

The present invention further provides 4-[5-(2-amino-ethanesulfonyl)-isoquinolin-7-yl]-phenol monohydrochloride hemihydrate in crystalline form having an X-ray powder diffraction pattern with intense peaks at 2θ=4.9, 14.8, and 10.2.

The present invention also provides 4-[5-(2-amino-ethanesulfonyl)-isoquinolin-7-yl]-phenol or a pharmaceutically acceptable salt thereof or hydrate thereof.

DETAILED DESCRIPTION OF THE INVENTION

Compounds of the present invention are inhibitors of Akt and are believed to be useful in the treatment of disorders related to Akt activity. Thus, compounds of the present invention are antineoplastic and/or antiviral agents.

The compounds of the present invention are useful for the treatment of neoplasms that exhibit defects in PTEN, neoplasms with deregulated PI3-Kinase activity, or neoplasms that exhibit elevated Akt activity. Akt inhibitors are believed to be useful in treating multiple myeloma (Hsu et al., *Blood* (2001) 98(9) 2853-2855); non small cell lung cancer (Balsara, *Carcinogenesis* (2004) 25(11) 2053-2059); glioblastoma (Koul, et al., *Mol. Cancer. Ther.* (2006) 5: 637-644); neuroblastoma (Li, et al., *Cancer Res.* (2005) 65(6), 2070-2075); melanoma (Dai, et al., *J. of Clin. Oncolog* (2005) 23(7), 1473-1482) and neoplasms of the prostate (Majumder, et al., *Oncogene* (2005) 24, 7465-7474); breast (Tokunaga, et al., *J. of Clin. Oncology* (Meeting Abstracts) (2005) 23(16S), 9500); ovaries (Cheung, et al., PNAS (1992) 89, 9267-9271; Yuan et al. (2000); Hu et al. (2000)); primary stomach or intestinal-type (Ang, et al., *Cancer Lett.* (2005) 225(1), 53-59); endometrium (Jin, et al., *British J. of Cancer* (2004) 91 1808-1812); thyroid (Ringel, et al., *Cancer Res.* (2001) 61(16), 6105-6111; De Vita, et al., *Cancer Res.* (2000) 60, 3916-3920); pancreas (Schliemen, et al., *Brit. J. of Cancer* (2003) 89, 2110-2115); lung (Massion, et al., *Am. J. Resp. Crit. Care Med.* (2004) 170, 1088-1094); or bladder (Rieger-Christ, et al., *Oncogene* (2004) 23(27), 4745-4753). Akt inhibitors are also believed to be useful in treating viruses such as hepatitis C and NS5A of hepatitis C (Mannova, et al., *J. Virol.* (2005) 79(14), 8742-8749; He et al. (2002)); rubella (Cooray, et al., *Virology J.* (2005) 2(1), 1-12); Tat protein of human immunodeficiency virus (HIV) (Borgatti et al. (1997)); Protein X of hepatitis B (Lee et al. (2001)), or human cytomegalovirus (HCMV) (Johnson et al. (2001)).

4-[5-(2-Amino-ethanesulfonyl)-isoquinolin-7-yl]-phenol forms pharmaceutically-acceptable acid addition salts with, for example, the physiologically-acceptable salts which are often used in pharmaceutical chemistry. Such salts are also part of this invention. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Preferable salts for 4-[5-(2-amino-ethanesulfonyl)-isoquinolin-7-yl]-phenol include the monohydrochloride and di-hydrochloride.

The intermediates described herein can form salts.

In addition to salts, the compounds of the present invention and the intermediates described herein can form a hydrate or a hydrate of the pharmaceutically acceptable salt.

A preferable compound is 4-[5-(2-amino-ethanesulfonyl)-isoquinolin-7-yl]-phenol. Yet another preferable compound is 4-[5-(2-amino-ethanesulfonyl)-isoquinolin-7-yl]-phenol di-hydrochloride. A more preferable compound is 4-[5-(2-amino-ethanesulfonyl)-isoquinolin-7-yl]-phenol monohydrochloride hemihydrate.

As used herein, the term "patient" refers to a mammal that is afflicted with one or more disorders associated with elevated Akt activity. It will be understood that the most preferred patient is a human. It is also understood that this invention relates specifically to the inhibition of mammalian Akt/PKB.

The terms "treatment," "treat," "treating," and the like, are meant to include effects such as decreasing and/or inhibiting the growth of neoplasms, the amplification and/or overexpression of Akt 1, Akt2, and/or Akt3, cell proliferation and survival, and/or viral replication.

As used herein, the term "effective amount" refers to an amount that inhibits Akt to an extent that provides a pharmacological effect.

The present invention also provides a pharmaceutical composition comprising 4-[5-(2-amino-ethanesulfonyl)-isoquinolin-7-yl]-phenol, or a pharmaceutically acceptable salt thereof, or hydrate thereof, and a pharmaceutically acceptable carrier, diluent, or excipient. Pharmaceutical compositions for the present invention include forms prior to dilution, such as a lyophilized form, and forms subsequent to dilution, such as a form ready for administration to a patient. The pH of these pharmaceutical compositions is from less than about 4.2 to greater than about 2.0. More preferably, the pH is from less than about 3.2 to greater than about 2.0. The most preferable pH is from less than about 2.8 to greater than about 2.0. A "pharmaceutically acceptable carrier, diluent, or excipient" is a medium generally accepted in the art for the delivery of biologically active agents to patients, e.g., mammals, preferably humans. Such carriers, diluents, or excipients are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers, diluents, or excipients can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, diluents, or excipients, and factors involved in their selection, are found in a variety of readily available sources. See, e.g., Remington: The Science and Practice of Pharmacy (A. Gennaro, et al., eds., 19 th ed., Mack Publishing Co., 1995).

The compounds of the present invention may be administered systemically, such as intravenously (e.g. by bolus or infusion), in dosage unit formulations of pharmaceutical compositions containing conventional non-toxic pharmaceutically acceptable carriers, diluents, or excipients.

For pharmaceutical compositions of 4-[5-(2-amino-ethanesulfonyl)-isoquinolin-7-yl]-phenol, the active ingredient will ordinarily be present in an amount of about 0.5 to 95% by weight based on the total weight of the composition. Appropriate coatings may be applied to increase palatability or to delay adsorption.

The therapeutically effective amounts of the compounds of the invention for treating the disorders described herein in a patient can be determined in a variety of ways known to those of ordinary skill in the art. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. For example, a typical daily dose may contain from about 1 mg to 1 g of the active ingredient.

The compounds of this invention may be prepared by employing the information provided herein, in addition to other standard manipulations that are known in the literature or exemplified in the experimental procedures.

The terms and abbreviations used herein have their normal meanings unless otherwise designated. For example "LC" refers to liquid chromatography; "dppb" refers to bis(diphenylphosphino)butane; Pd(OAc)$_2$ refers to palladium acetate; "DMF" refers to N,N-dimethylformamide; "DMSO" refers to dimethylsulfoxide; "Et$_2$O" refers to diethyl ether; "EtOAc" refers to ethyl acetate; "TFA" refers to trifluoroacetic acid; MeOH refers to methanol.

PREPARATIONS

Preparation 1

2-[7-(4-Methoxy-phenyl)-isoquinoline-5-sulfonyl]-ethylamine di-hydrochloride

Treat a slurry of {2-[7-(4-methoxy-phenyl)-isoquinoline-5-sulfonyl]-ethyl}-carbamic acid tert-butyl ester (11.00 g, 24.85 mmol) in anhydrous MeOH (150 mL) with 4N HCl in dioxane (350 mL). Stir the resulting reaction mixture at room temperature overnight, then concentrate in vacuo to ½ volume and treat with excess EtOAc, causing a yellow solid to precipitate. Recover the resulting solid by vacuum filtration under an N$_2$ atmosphere; wash with EtOAc and dry under vacuum (under an N$_2$ atmosphere) to afford the title compound (10.23 g, 99% yield) as a yellow solid: MS (ES): m/z 343.0 (M$^+$+H).

Preparation 2

7-Bromo-isoquinoline-5-sulfonic Acid

Add fuming H$_2$SO$_4$ (2,000 mL, 21.33 mol; 26-29.5% free SO$_3$) to a 5-L round bottom flask, equipped with a mechanical stirrer, reflux condenser, N₂ line, and thermometer. Cool the fuming $H_2SO_4$ to ~10° C. with an ice/acetone bath, then add 7-bromoisoquinoline HCl (500.00 g, 2.04 mol) portion-wise, keeping the temperature of the reaction mixture below ~15-20° C. Upon complete addition of 7-bromoisoquinoline HCl, heat the resulting reaction mixture at ~100° C. overnight. Cool the reaction mixture to room temperature, then slowly pour into a stirring solution of ice $H_2O$. Recover the resulting precipitate by vacuum filtration, washing with $H_2O$, then $Et_2O$, and dry under vacuum filtration, followed by drying in a drying oven under reduced pressure at ~35° C. to afford the title compound (501.42 g, 85% yield) as an off-white solid: TOF-MS [ES+; m/z] 287.9331/287.9330.

Preparation 3

7-(4-(Methoxy-phenyl)-isoquinoline-5-sulfonic Acid

Treat a solution of 7-bromo-isoquinoline-5-sulfonic acid (150.00 g, 0.520 mol) and 4-methoxyphenylboronic acid (90.87 g, 0.598 mol) in DMF (1,400 mL) and MeOH (375 mL) with 2M aqueous $Na_2CO_3$ (652 mL). Deoxygenate the resulting slurry 3× with $N_2$, then add Pd(OAc)₂ (2.33 g, 0.0104 mol) and dppb (5.54 g, 0.0130 mol). Heat the resulting reaction mixture at ~70° C. for 3 hr, then allow to cool to room temperature overnight. Dilute the reaction mixture with $H_2O$ (4,000 mL) and adjust the pH to ~pH 2 with 5N aqueous HCl. Allow the resulting slurry to stir at room temperature for 30 min, then recover the brown solid by vacuum filtration, washing with $H_2O$ and drying under vacuum filtration. Dissolve the brown solid in DMF (1,000 mL) and 2M aqueous $Na_2CO_3$ (650 mL) and filter the resulting solution through a pad of Celite®, washing with DMF (400 mL)/$H_2O$ (400 mL). Treat the filtrate with 5N aqueous HCl to adjust the pH to ~pH 2. Allow the resulting slurry to stir at room temperature for 30 min, then recover the solid by vacuum filtration, washing with $H_2O$ and drying under vacuum filtration overnight. Dissolve the solid in DMF (1,000 mL) and 2M aqueous $Na_2CO_3$ (1,000 mL) again and treat the resulting solution with Celite® to create a slurry. Stir the resulting slurry at room temperature for 30 min, then filter through a pad of Celite®, washing with $H_2O$. Treat the filtrate with 5N aqueous HCl to adjust the pH to ~pH 2. Stir the resulting slurry at room temperature for 30 min, then recover the solid by vacuum filtration, washing with $H_2O$ and drying under vacuum filtration overnight. Crush the solid, then wash with EtOAc, drying under vacuum filtration overnight, followed by drying in a drying oven under reduced pressure at ~35° C. to afford the title compound (136.79 g, 83% yield) as a yellow solid: TOF-MS [ES⁺; m/z] 316.0624/316.0643. Anal. Calcd. For $C_{16}H_{13}NO_4S$: C, 60.94; H, 4.15; N, 4.44; S, 10.16. Found C, 60.76; H, 4.13; N, 4.50; S, 9.90.

Preparation 4

7-(4-Methoxy-phenyl)-isoquinoline-5-sulfonyl Chloride

To a slurry of 7-(4-methoxy-phenyl)-isoquinoline-5-sulfonic acid (12.13 g, 38.5 mmol) in 1,2-dichloroethane (200 mL) and DMF (2.99 mL, 38.5 mmol) add oxalyl chloride (26.8 mL, 308 mmol) dropwise. Mechanically stir the slurry under nitrogen atmosphere while heating at 60-65° C. for 4 hr. Cool the slurry to −10° C. Wait for 30 min then filter. Wash the yellow solid with 20% ether/dichloromethane and dry under a nitrogen atmosphere affording the title compound (14.8 g) as a yellow powder.

Preparation 5

7-(4-Methoxy-phenyl)-isoquinoline-5-thiol Sodium Salt

A. To a slurry of 7-(4-methoxy-phenyl)-isoquinoline-5-sulfonyl chloride (4.0 g, 12 mmol) in dioxane (40 mL) add tricarboxy ethyl phosphine hydrochloride (13.73 g, 48 mmol) and water (10 mL). Heat the mixture to 100° C. and stir for 3 hr. Cool the mixture in an ice bath, and add NaOH (5 N, 60 mL) slowly via a pipette. Filter and air dry the pale yellow precipitate to afford the title compound (3.2 g, 95%). Mass spectrum (LCMS) m/z=266.2 (M−Na⁺).

Alternatively, the title compound can be made as follows:

B. (i) Deoxygenate a solution of 7-(4-methoxy-phenyl)-isoquinoline-5-sulfonic acid (100.00 g, 0.317 mol) in anhydrous toluene (2,500 mL) 3× with $N_2$, then treat with Ph₃P (332.58 g, 1.268 mol), I₂ (80.46 g, 0.317 mol), and Bu₃N (152.00 mL, 0.638 mol). Allow the resulting reaction mixture to reflux for 1 hour under $N_2$, then cool to room temperature overnight while bubbling air into the reaction mixture. Treat the reaction mixture with an aqueous solution of 1N NaOH (500 mL), then stir the resulting reaction mixture at room temperature overnight while bubbling air into the reaction mixture. Recover the resulting tan precipitate by vacuum filtration. Wash with a 1/1 solution of THF/$Et_2O$, then dry under vacuum filtration to afford bis-(7-(4-methoxy-phenyl)-isoquinoline-5)-disulfide (72.50 g, 86% yield) as a light tan solid: ¹H NMR (400 MHz, DMSO) δ 9.39 (s, 2H), 8.51 (d, 2H), 8.41 (s, 2H), 8.11 (d, 2H), 8.00 (d, 2H), 7.53 (d, 4H), 6.94 (d, 4H), 3.78 (s, 6H).

B. (ii.) Treat a slurry of bis-(7-(4-methoxy-phenyl)-isoquinoline-5)-disulfide in anhydrous THF (850 mL) with NaBH₄ (2.84 g, 75.07 mmol). Heat the resulting reaction mixture at ~35° C. under $N_2$ for ~1 hour, then heat at ~45° C. under $N_2$ for ~1 hour.

Preparation 6

7-(4-Methoxy-phenyl)-isoquinoline-5-sodium Sulfinate

To 7-(4-methoxy-phenyl)-isoquinoline-5-sulfonyl chloride (1.48 g, 4 mmol) in water (10 mL), add $Na_2SO_3$ (1.01 g, 8 mmol) and $NaHCO_3$ (1.01 g, 12 mmol). Heat the mixture to 100° C. and stir for 1 hr. Cool the reaction mixture to room temperature, and remove water under reduced pressure. Add methanol (40 mL) to the residue, stir for 10 min. Filter the white solid, wash with methanol, and combine filtrates. Concentrate to give the title compound (1.1 g).

Preparation 7

(3,5-Dichloro-benzylidene)-(2,2-diethoxy-ethyl)-amine

The 2,2-Diethoxy-ethylamine (1852.5 g; 1.00 equiv; 13.63 moles), 3,5-dichloro-benzaldehyde (2453 g; 1.00 equiv; 13.60 moles), and Toluene (12 L) is charged to a 22 L flask equipped with a Dean Stark trap, condenser, nitrogen inlet, overhead stirring, and thermocouple. The light yellow reaction is warmed to reflux. Solvent begins distilling at 88° C. A total of ~650 mL distillate (~240 mL of water) is collected. The temperature is increased to 114° C. during the distillation. NMR after 2 hr at reflux shows the product. The heat is shut off after 2.5 hr. The solution is gravity filtered into a carboy through fluted filter paper to remove a few particulates (including a small section of glass tubing, which is most likely from the 3,5-dichloro-benzaldehyde). The filtered solution is concentrated using Buchi flask with the water bath set at 45° C. Once the solvent stops coming over, the temperature is increased to 70° C. with full vacuum and held for ~1.5 hr to remove any residual toluene. The weight of (3,5-Dichloro-benzylidene)-(2,2-diethoxy-ethyl)-amine is 4059.3 g (102.9% of theory). Mass Spectrum (LCMS) m/z=291.2) (M+H$^+$)

Preparation 8

5,7-Dichloro-isoquinoline Hydrochloride

Triflic acid (2.97 L; 33.52 moles; 5.03 kg) is charged to a 12 L flask equipped with a Dean Stark trap, overhead stirring, condenser, nitrogen inlet, 3 L addition funnel (buffered from the flask via a condenser), and thermocouple. The triflic acid is heated to 120° C. (3,5-Dichloro-benzylidene)-(2,2-diethoxy-ethyl)-amine (1350.5 g; 1.00 equiv; 4.65 moles) is diluted with dichloromethane (1350 mL) and is charged to the addition funnel. The addition is started with the temperature at 119° C. The addition is completed over 90 minutes holding the temperature at 120° C. Approximately 1500 mL of distillate is collected during the addition. Area % HPLC 45 minutes after the addition is completed and indicates 94.14% product and 4.86% (3,5-Dichloro-benzylidene)-(2,2-diethoxy-ethyl)-amine. The heat is shut off after 1.5 hr. The reaction is cooled to ~80° C. At this point the flask is placed in an ice water bath and is cooled further. Add methanol (2.7 L) with the reaction at 9° C. The addition is completed over 60 minutes. The maximum temperature is 27° C. Some solid forms during the methanol addition. This slurry is transferred in portions to a 2 L addition funnel and is added to a solution of ammonium hydroxide (5.1 L; 36.67 moles; 4.59 kg) and water (5.1 L) in a 22 L flask, chilled in ice water to <2° C. The addition funnel has a Teflon® tube extension to prevent the material from running down the side of the flask, which can lead to a more oily solid adhering to the flask wall. The material is added in small slugs to prevent the addition funnel from plugging due to the solids. The addition is completed over 35 minutes including a methanol (900 mL) rinse of the flask and addition funnel. The maximum temperature is 26° C. A brown solid forms. The slurry is cooled to 14° C. The solid is filtered onto a polypropylene pad. The solid is washed with 2×4 L and 1×2 L of water. The solid is then washed with 2 L of heptane to aid drying. The solid is dried in vacuo at 50° C. to a weight of 999.0 g (108.4% of theory). The 5,7-dichloro-isoquinoline (997 g; 1.00 equiv; 5.03 moles) and ethanol (14.97 L) are charged to a 22 L flask equipped with an addition funnel, nitrogen inlet, overhead stirring, and thermocouple. The brown slurry is stirred at ambient temperature (22° C.). The acetyl chloride (1180 mL; 16.58 moles; 1.30 kg) is charged to the addition funnel. This is added to the flask dropwise. The brown slurry darkens. The solid appears to mostly dissolve by adding 100-200 mL of the acetyl chloride. A complete solution does not form. Solid reappears as the addition continues. The addition is completed over 45 minutes. The maximum temperature is 43° C., which is reached about halfway into the addition and is maintained with cool water in the bath. A sample of the reaction is removed after ~¾ of the acetyl chloride is added for NMR. Since the sample appears to be the salt, excess acetyl chloride is likely not needed. The slurry is stirred and is allowed to cool. After 40 minutes, the temperature is 30° C. The slurry is cooled to <2° C. and is held for 1.5 hr in an ice-water bath. The slurry is filtered. The solid is washed with 2×1.3 L of chilled ethanol. The wet cake weight is 811.4 g. The solid is dried in vacuo at 50° C. The dry weight is 648.4 g. This represents a 61.0% yield. Mass Spectrum (LCMS) m/z=199.05) (M+H$^+$)

Preparation 9

[2-(7-Chloro-isoquinolin-5-ylsulfanyl)-ethyl]-carbamic Acid Tert-butyl Ester

Potassium carbonate (1952 g; 14.12 moles) is charged to a 22 L flask equipped with overhead stirring, addition funnel, nitrogen inlet, and thermocouple. Dimethylformamide (4 L) is added. The 5,7-dichloro-isoquinoline hydrochloride (646.1 g; 1.00 equiv; 2.76 moles) is added in portions and along with DMF (330 mL). The Boc-Cysteamine (514 g; 1.05 equiv; 2.90 moles) is dissolved in dimethylformamide (1520 mL) and is charged to the addition funnel. The mixture is warmed to 60° C. Nitrogen is purged through the head space for 15 minutes while the mixture is warming. The Boc-Cysteamine solution is added over 2 hrs and 15 minutes at 60° C. HPLC 1 hour and 20 minutes after the addition indicates 28.1% starting material, 67.26% product, 4.22% isomer, and 0.25% bis. The reaction is warmed to 75° C. The HPLC data in Table A is collected at 75° C.

TABLE A

Reaction HPLC Data for the Preparation of [2-(7-chloro-isoquinolin-5-ylsulfanyl)-ethyl]-carbamic acid tert-butyl ester

| Time at 75° C. | % 5,7-dichloro-isoquinoline HCl | % [2-(7-Chloro-isoquinolin-5-ylsulfanyl)-ethyl]-carbamic acid tert-butyl ester | % isomer | % bis substituted |
| --- | --- | --- | --- | --- |
| 30 minutes | 2.75 | 90.27 | 5.54 | 1.44 |
| 1 hour | 0.93 | 91.39 | 5.52 | 2.16 |
| 1.5 hours | 0.20 | 91.25 | 5.32 | 3.23 |

After 1.5 hours the mantle is replaced with a cooling bath. The reaction is cooled to 20-25° C. The solid is filtered and is washed with DMF (2×810 mL). The DMF solution is diluted with MTBE (5.15 L) and 5% LiCl (5.15 L). After stirring in a 50 L bottom outlet flask, the layers are separated. The aqueous layer is extracted with MTBE (2.9 L). The MTBE layers are combined and washed with 5% LiCl (2×2.9 L). The MTBE layer is gravity filtered through fluted paper and is concentrated using Buchi flask with the water bath set at 35° C. to give 892.7 g (95.6% of theory, uncorrected) of [2-(7-chloro-isoquinolin-5-ylsulfanyl)-ethyl]-carbamic acid tert-butyl ester. Mass Spectrum (LCMS) m/z=339.85) (M+H$^+$).

Preparation 10

[2-(7-Chloro-isoquinoline-5-sulfonyl)-ethyl]-carbamic Acid Tert-butyl Ester

The [2-(7-Chloro-isoquinolin-5-ylsulfanyl)-ethyl]-carbamic acid tert-butyl ester (700 g; 1.00 equiv; 2.07 moles) is dissolved in isopropyl alcohol (10.53 L) by rotating on Buchi flask with the water bath set at 50° C. Mequinol (12.29 g; 98.01 mmoles; 12.29 g), sodium tungstate dihydrate (31.4 g; 95.20 mmoles), the [2-(7-Chloro-isoquinolin-5-ylsulfanyl)-ethyl]-carbamic acid tert-butyl ester solution, isopropyl alcohol (2.77 L), water (3.38 L), and acetic acid (123 mL; 2.15 moles; 128.90 g) are charged to a 22 L flask equipped with a condenser, nitrogen inlet, overhead stirring, addition funnel, and thermocouple. Addition of the water causes the brown solution to become slightly milky looking. The reaction is warmed to 50° C. using a hot water bath. Hydrogen peroxide (607 mL; 5.94 moles; 673.77 g) is added over 1 hour. During the addition, the temperature is maintained at 50-55° C. by the hydrogen peroxide addition rate and by adding cool or warm water to the bath as needed. The reaction is still milky brown. The reaction temperature is 54° C. at the end of the addition and is maintained at 53-57° C. using the warm water bath. HPLC 10 minutes after the addition indicates 24.69% peak at 2.89 min., 65.57% product, 5.03% isomer, 4.33% bis, and 0.18% peak at 3.05 min. HPLC 2 hours after the addition indicates 0.06% sulfoxide, 1.27% peak at 3.046 min., 88.10% product, 4.61% isomer, and 5.79% bis. The bath is drained and replaced with ice water to cool the reaction. When the reaction temperature reaches 27° C., the peroxide is quenched by adding 9% sodium bisulfite solution (250 mL). No increase in temperature is observed. Peroxide test strips and starch iodide paper indicate no peroxide remaining. Water (5.64 L) is added over 15-20 minutes. The temperature increases from 18 to 24° C. during the addition. The mixture is stirred at ambient temperature overnight. The slurry is cooled in an ice water bath to <5° C. and held. Quantitative HPLC of the supernate over time indicated the crystallization is complete after 1.5 hours at <5° C. The solid is filtered and washed with water (2×2 L). The wet cake weight was 831 g. The solid is dried in vacuo at 50° C. The weight of dry [2-(7-Chloro-isoquinoline-5-sulfonyl)-ethyl]-carbamic acid tert-butyl ester is 531 g (69.31% of theory, uncorrected). Mass Spectrum (LCMS) m/z=371.85) (M+H$^+$)

Preparation 11

(2-{7-[4-(Tetrahydro-pyran-2-yloxy)-phenyl]-isoquinoline-5-sulfonyl}-ethyl)-carbamic Acid Tert-Butyl Ester The 60 L reactor is charged with PEPPSI™ (Pyridine-Enhanced Precatalyst Preparation Stabilization and Initiation; 51.0 g; 74.9 mmoles), [2-(7-Chloro-isoquinoline-5-sulfonyl)-ethyl]-carbamic acid tert-butyl ester (1.383 kg; 3.729 moles), phenyl boronic acid (895 g; 4.03 moles), $K_2CO_3$ (1.039 kg; 7.518 moles), and ethanol (15 L) under a nitrogen purge. Initially 12 L of ethanol is added to the reactor and the remaining 3 L was used to rinse in the other charges. The reaction is warmed to reflux (78° C.). HPLC indicates a complete reaction after ½ hour. The reaction is cooled to 59° C. using the Huber® circulator. Water (8.7 L) is added to the reaction over 18 minutes. The temperature is decreased from 59° C. to 42° C. during the water addition. The reaction is cooled using the Huber® circulator from 42° C. to 0° C. over 1 hour. The slurry is held at 0° C. for 1 hour. The solid is filtered using a polypropylene pad and washed with 1:1 ethanol:water (3.7 L; chilled). The solid is dried on the filter overnight. The solid is then dried in vacuo at 60° C. for 22 hours. The dry weight of the solid is 2.171 kg. The Pd level in the crude (2-{7-[4-(tetrahydro-pyran-2-yloxy)-phenyl]-isoquinoline-5-sulfonyl}-ethyl)-carbamic acid tert-butyl ester is 2196 mcg/g and the solid contains 6.9% water by KF. A 50 L bottom outlet flask is charged with dichloromethane (4 L). The crude (2-{7-[4-(tetrahydro-pyran-2-yloxy)-phenyl]-isoquinoline-5-sulfonyl}-ethyl)-carbamic acid tert-butyl ester is charged to the 50 L flask and rinsed in with dichloromethane (1 L). $Na_2SO_4$ (1.9 kg) is charged and rinsed in with dichloromethane (0.1 L). Darco G-60® (3.8 kg) is charged to a 20 L Büchi flask and slurried in dichloromethane (12 L). This slurry is transferred to the 50 L flask and rinsed in with dichloromethane (4.9 L). The mixture is stirred for 2 hrs at ambient temperature. A 50 cm stainless steel filter is fitted with a polypropylene pad and charged with Hyflo Super Cel® (1.7 kg). The Hyflo Super Cel® pad is rinsed with dichloromethane (2 L). The contents of the 50 L flask are filtered onto the Hyflo Super Cel® pad. The flask and filter cake are rinsed with dichloromethane (22 L). The filtrate is charged to the 60 L reactor through a 0.45 micron cartridge filter. The contents of the reactor are warmed and concentrated by distillation under slight vacuum (~640 mm Hg). Approximately 33 L of distillate is collected over 2 hrs at 35-37° C. Ethanol (10 L) is added. The vacuum is adjusted slowly down to 280 mm Hg while continuing the distillation. Once the vacuum is reached, the temperature is increased to maintain the distillation. Once the volume in the reactor reaches ~10 L, ethanol (6.5 L) is added at such a rate to maintain the volume in the reactor while distilling out solvent. The distillation is stopped once all the ethanol is added. The final volume is ~10 L. The temperature at the end of the distillation is 56° C. The slurry that forms during the solvent exchange is cooled to 20° C. and held overnight. The slurry is filtered. The solid is washed with 1:1 ethanol:water (1.8 L). The wet cake weight is 1.878 kg. The solid is dried in vacuo at 50° C. to give 1.2306 kg (64.36% yield) (2-{7-[4-(tetrahydro-pyran-2-yloxy)-phenyl]-isoquinoline-5-sulfonyl}-ethyl)-carbamic acid tert-butyl ester. Mass Spectrum (LCMS) m/z=513.62) (M+H).

EXAMPLES

Example 1

4-[5-(2-Amino-ethanesulfonyl)-isoquinolin-7-yl]-phenol di-hydrochloride Salt

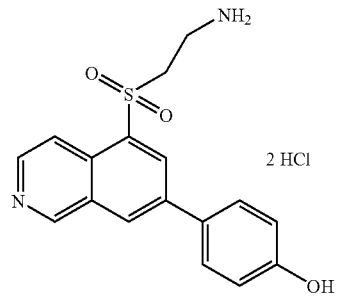

A. {2-[7-(4-Methoxy-phenyl)-isoquinolin-5-ylsulfanyl]-ethyl}-carbamic Acid Tert-Butyl Ester To 7-(4-methoxy-phenyl)-isoquinoline-5-thiol sodium salt (0.29 g, 1 mmol) in acetone (10 mL), add (2-bromo-ethyl)-carbamic acid tert-butyl ester (0.22 g, 1 mmol) and potassium carbonate (0.14 g, 1 mmol). Stir the mixture at room temperature for 4 hr then load onto a silica gel column, and elute with 65% ethyl acetate in hexane to afford the title compound (0.35 g, 86%). Mass spectrum (LCMS) m/z=355.2 (M+H$^+$).

B. {2-[7-(4-Methoxy-phenyl)-isoquinoline-5-sulfonyl]-ethyl}-carbamic Acid Tert-Butyl Ester To a solution of {2-[7-(4-methoxy-phenyl)-isoquinolin-5-ylsulfanyl]-ethyl}-carbamic acid tert-butyl ester (0.35 g, 0.85 mmol) in acetic acid (8 mL), add water (2 mL). Cool the mixture to 0° C. in an ice bath. Add a solution of $KMnO_4$ (0.27 g, 1.7 mmol) in water (2 mL) dropwise over a period of 5 min. After the addition, stir the reaction mixture at 0° C. for 30 min. Add $H_2O_2$ (30% in water) dropwise until the brown color disappears. Partition the mixture between ethyl acetate (50 mL) and saturated sodium bicarbonate (40 mL). Separate the organic layer, dry over sodium sulfate; filter and concentrate. Chromatograph the residue on a silica gel column with 66% ethyl acetate in hexane to afford the title compound (0.245 g) as white solid. Mass spectrum (LCMS) m/z=433.2 (M+H$^+$).

C. 4-[5-(2-Amino-ethanesulfonyl)-isoquinolin-7-yl]-phenol di-hydrochloride

To {2-[7-(4-methoxy-phenyl)-isoquinoline-5-sulfonyl]-ethyl}-carbamic acid tert-butyl ester (0.22 g, 0.51 mmol) in dichloroethane (10 mL), add BBr$_3$ (1.0 M in dichloromethane, 3.0 mL) at −20° C. After the addition, stir the reaction mixture at −20° C. for 2 hr, slowly warm to room temperature and stir at room temperature for 2 hr. Add methanol (5 mL) to quench excess BBr$_3$. Evaporate the solvent under reduced pressure, and purify the residue via Reverse Phase HPLC (0-100% acetonitrile:water with 0.01% TFA) to afford 4-[5-(2-amino-ethanesulfonyl)-isoquinolin-7-yl]-phenol as the TFA salt (0.18 g). Then, convert 0.12 g of the TFA salt to the di-hydrochloride salt by adding 2 mL of saturated aqueous sodium bicarbonate to the TFA salt and stir overnight in order to convert the TFA salt to the free base. Filter the free base. Wash the free base, first with water, then with diethyl ether. Dry the solid. Then, suspend the solid in MeOH. Add 0.2 mL of concentrated aqueous HCl and stir for 1 hr. Concentrate the solvent under reduced pressure to provide the dihydrochloride salt. (0.10 g). Mass spectrum (LCMS) m/z=329.0 (M+H$^+$)

Example 2

4-[5-(2-Amino-ethanesulfonyl)-isoquinolin-7-yl]-phenol

To {2-[7-(4-methoxy-phenyl)-isoquinoline-5-sulfonyl]-ethyl}-carbamic acid tert-butyl ester (25.00 g, 56.49 mmol) in dichloromethane (1 L) at 0° C. add BBr$_3$ (1.0 M in dichloromethane, 200 mL, 200 mmol) over 40 min with vigorous overhead stirring. Remove the cooling bath and stir at room temperature overnight. Cool to 0° C. and add methanol (500 mL) dropwise over 1 h. Filter the resulting slurry, rinse the flask with dichloromethane (100 mL) and wash the solids with the rinse. Wash the solids with additional dichloromethane (150 mL) and dry under vacuum filtration. Slurry the solids in methanol (400 mL) with stirring, then concentrate under vacuum to a thin paste. Add additional methanol (400 mL) and further slurry the solids with stirring. Concentrate the slurry under vacuum to dryness, and dry the solids overnight under vacuum. Pulverize the solids to a powder and slurry in methanol (1 L). Add Amberlyst® A-21 resin (75 g) and stir until the powder is dissolved. Filter the resin, slurry the filtered resin in methanol (220 mL) and filter the resin again, combining the filtrates. Wash the filtered resin with methanol (100 mL) and add this wash to the filtrates. Combine the filtrates with ethanol (200 mL) and concentrate the mixture under vacuum to a volume of about 200 mL to afford a slurry. Add ethanol (400 mL), warm the slurry to 50° C. for about 15 min, then concentrate under vacuum to a volume of about 200 mL. Cool the slurry to room temperature, filter and rinse the filter cake with ethanol (2×15 mL), then dry under vacuum to afford the title compound (10.22 g, 55%) as a tan solid. Mass spectrum (LCMS) m/z=329.0 (M+H$^+$).

Example 3

4-[5-(2-amino-ethanesulfonyl)-isoquinolin-7-yl]-phenol

Cool a slurry of 2-[7-(4-methoxy-phenyl)-isoquinoline-5-sulfonyl]-ethylamine dihydrochloride (9.5504 g, 22.99 mmol) in anhydrous CH$_2$Cl$_2$ (400 mL) to ~5° C. with an ice/H$_2$O bath, then treat the cold slurry with a dropwise addition of a 1.0 M solution of BBr$_3$ in CH$_2$Cl$_2$ (92.00 mL, 92.00 mmol). Upon complete addition of the BBr$_3$, remove the cold bath and allow the resulting reaction mixture to stir under N$_2$ at room temperature overnight. Quench the resulting reaction mixture with MeOH, then concentrate in vacuo to give a residue. Dissolve the resulting residue in MeOH (200 mL) and concentrate in vacuo to give a residue. Repeat the above 3 times, then slurry the residue in Et$_2$O (300 mL) and treat with saturated aqueous NaHCO$_3$ until ~pH7 is reached. Recover the resulting solid by vacuum filtration, then dissolve in a 3/1 solution of CHCl$_3$/MeOH. Saturate the filtrate with NaCl, then extract with a 3/1 solution of CHCl$_3$/MeOH (2×400 mL each). Dry the combined organics over MgSO$_4$, filter, then concentrate in vacuo to give a solid/residue. Slurry the solid/residue in a small amount of MeOH (20 mL) and excess hexanes, then recover the resulting solid by vacuum filtration, washing with hexanes and drying under vacuum filtration to give (7.60 g) of a light-yellow solid. Slurry the light-yellow solid (7.60 g) in anhydrous CH$_2$Cl$_2$ (400 mL) and cool to ~5° C. with an ice/H$_2$O bath, then treat with a dropwise addition of a solution of 1.0 M BBr$_3$ in CH$_2$Cl$_2$ (70.00 mL, 70.00 mmol). Upon complete addition of the BBr$_3$, remove the cold bath and allow the resulting reaction mixture to stir at room temperature under N$_2$ for 4 hours. Add an additional amount of 1.0 M BBr$_3$ in CH$_2$Cl$_2$ (70.00 mL, 70.00 mmol) dropwise to the reaction mixture, then allow the resulting reaction mixture to stir at room temperature under N$_2$ overnight. Heat the reaction at ~40° C. for ~1 hour, then treat with a dropwise addition of additional 1.0 M BBr$_3$ in CH$_2$Cl$_2$ (23.00 mL, 23.00 mmol). Heat the resulting reaction mixture at ~40° C. for ~2 hours, then quench with MeOH and concentrate in vacuo to give a residue. Dissolve the resulting residue in MeOH (200 mL) and concentrate in vacuo to give a yellow residue. Repeat the above 3 times. Treat the yellow residue with saturated NaHCO$_3$ to adjust the pH to ~7, then recover the resulting solid by vacuum filtration. Pre-absorb the solid on silica gel, then semi-purify by column chromatography (ISCO 330 g silica gel, neat CH$_2$Cl$_2$ to 5% of 2N NH$_4$/MeOH in CH$_2$Cl$_2$ to 10% of 2N NH$_4$/MeOH in CH$_2$Cl$_2$) to give a solid. Pre-absorb the solid on silica gel, then re-purify by column chromatography (ISCO 330 g silica gel, neat CH$_2$Cl$_2$ to 5% of 2N NH$_4$/MeOH in CH$_2$Cl$_2$ to 10% of 2N NH$_4$/MeOH in CH$_2$Cl$_2$) to give a solid. Pre-absorb the solid on silica gel, then re-purify by column chromatography (ISCO 330 g silica gel, neat CH$_2$Cl$_2$ to 5% of 2N NH$_4$/MeOH in CH$_2$Cl$_2$ to 10% of 2N NH$_4$/MeOH in CH$_2$Cl$_2$ to 15% of 2N NH$_4$/MeOH in CH$_2$Cl$_2$) to give a solid. Pre-absorb the solid on silica gel, then re-purify by column chromatography (ISCO 330 g silica gel, 5% MeOH in CHCl$_3$ to 10% MeOH in CHCl$_3$ to 20% MeOH in CHCl$_3$ to 30% MeOH in CHCl$_3$) to give (6.85 g, 90.8% yield) of the title compound as a yellow solid: MS (ES$^+$, m/z): 329.0 (M+1).

Example 4

4-[5-(2-Amino-ethanesulfonyl)-isoquinolin-7-yl]-phenol Monohydrochloride, Unknown Hydrate State

Place 4-[5-(2-amino-ethanesulfonyl)-isoquinolin-7-yl]-phenol (171.8 mg) in a vial along with 15 mL of 95% EtOH. Place vial on hot plate set to 80° C. while stirring the solution to dissolve the compound. Since little to no dissolution occurs, add one molar equivalent of HCl (0.52 mL of 1N HCl in water) to dissolve the solid and result in a bright yellow solution. Less than a minute after the HCl addition, solid formation begins and increases with time. After ~2 hours at 80° C., remove the sample from the heat and allow it to stir overnight at RT. Collect solid using vacuum filtration through filter paper. After air drying overnight, recover 107.8 mg of the title compound (63% yield). X-ray powder diffraction: angle, 2θ (% intensity): 11.8 (100.0); 16.6 (52.9); 8.2 (43.4).

Example 5

4-[5-(2-Amino-ethanesulfonyl)-isoquinolin-7-yl]-phenol Monohydrochloride Hemihydrate

A. Preparation of seed material. To a slurry of 4-[5-(2-Amino-ethanesulfonyl)-isoquinolin-7-yl]-phenol (0.2509 g, 0.764 mmol) in ethanol (5 mL) add aqueous HCl (1 M, 0.765 mL, 0.765 mmol). Heat the resulting mixture to reflux overnight. Cool to room temperature and vacuum filter the slurry. Rinse the solids with ethanol, and dry under vacuum filtration to afford 0.1842 g of a yellow solid.

B. 4-[5-(2-Amino-ethanesulfonyl)-isoquinolin-7-yl]-phenol monohydrochloride hemihydrate To a slurry of 4-[5-(2-Amino-ethanesulfonyl)-isoquinolin-7-yl]-phenol (1.75 g, 5.33 mmol) in ethanol (35 mL) add aqueous HCl (1 M, 5.33 mL, 5.33 mmol). Heat the mixture to reflux and add water (2.5 mL) to obtain a solution. Cool the solution to 60° C. and seed with about 2 mg of the yellow solid obtained from A. above to obtain a slurry. Cool to room temperature and stir overnight. Vacuum filter the slurry and rinse the filter cake with ethanol, then dry under vacuum filtration to afford 1.331 g (67%) of the title compound as a yellow solid. Mass spectrum (LCMS) m/z=329.0 (M+H$^+$). Karl Fischer: 3.00%. X-ray powder diffraction: angle, 2θ (% intensity): 4.9 (47.3); 14.8 (55.8); 10.2 (45.5).

Example 6

4-[5-(2-Amino-ethanesulfonyl)-isoquinolin-7-yl]-phenol di-hydrochloride Salt

Slurry 4-[5-(2-Amino-ethanesulfonyl)-isoquinolin-7-yl]-phenol (16.57 g, 50.45 mmol) in methanol (500 mL). Separately, prepare a solution of HCl in methanol by adding acetyl chloride (12.60 mL, 177.05 mmol) to methanol (165 mL). Add the solution of HCl in methanol dropwise at room temperature over 30 min to the slurry of 4-[5-(2-Amino-ethanesulfonyl)-isoquinolin-7-yl]-phenol in methanol. Stir for 30 min, then add ethyl acetate (600 mL) dropwise over 1 hour. Stir for 30 min, then filter the solids and wash with ethyl acetate (2×100 mL). Dry solids in vacuo at 50° C., then further dry in vacuo at room temperature with slow administration of nitrogen to afford the title compound (18.3 g, 90%). Mass spectrum (LCMS) m/z=329.0 (M+H$^+$).

Example 7

4-[5-(2-Amino-ethanesulfonyl)-isoquinolin-7-yl]-phenol di-hydrochloride Salt

The 60 L reactor is charged with ethanol (24 L) and (2-{7-[4-(Tetrahydro-pyran-2-yloxy)-phenyl]-isoquinoline-5-sulfonyl}-ethyl)-carbamic acid tert-butyl ester (2.652 kg; 5.173 moles). The (2-{7-[4-(Tetrahydro-pyran-2-yloxy)-phenyl]-isoquinoline-5-sulfonyl}-ethyl)-carbamic acid tert-butyl ester is rinsed in with ethanol (2.6 L). Hydrochloric acid solution (31.9%; 1780 g; 15.6 moles) is diluted with water (1.42 L). This HCl solution is charged to the reactor and rinsed in with water (0.2 L). The reaction is warmed to 70° C. A yellow solution forms around 30° C. and a yellow slurry reforms near 70° C. The reaction is held at 70° C. for ½ hr and then is warmed up to reflux (78° C.). HPLC indicates a complete reaction after 1.5 hrs at reflux. Water (14.5 L) is added to the reaction over 13 minutes. The temperature drops to 69° C. The reaction is heated back to reflux (80° C.) and a solution forms. The reaction is cooled to 68° C. and solid begins forming. The reaction is held at 68° C. for ½ hr and then cools to 2° C. over 1.5 hrs. The slurry is held at 1-2° C. for 1 hr. The solid is filtered and washed with ethanol (4.6 L). The wet cake weight is 3.236 kg. The solid is dried in vacuo at 50° C. to give 2.106 kg (101.4% of theory) 4-[5-(2-amino-ethanesulfonyl)-isoquinolin-7-yl]-phenol di-hydrochloride salt. Mass Spectrum (LCMS) m/z=402.31) (M+H).

Example 8

4-[5-(2-Amino-ethanesulfonyl)-isoquinolin-7-yl]-phenol Monohydrochloride Hemihydrate

The ethanol and sodium hydroxide solutions used for this example are filtered through a 0.22 micron cartridge filter. The water used is purified water with endotoxin control. Ethanol (8 L) and 4-[5-(2-amino-ethanesulfonyl)-isoquinolin-7-yl]-phenol di-hydrochloride salt (841.6 g; 2.097 moles) are charged to a 22 L flask equipped with overhead stirring, condenser, nitrogen inlet, heating mantle, thermocouple, and addition funnel. The 4-[5-(2-amino-ethanesulfonyl)-isoquinolin-7-yl]-phenol di-hydrochloride salt is rinsed in with ethanol (3.28 L). The reaction is warmed to 55° C. Sodium hydroxide solution (1100 mL; 1.91 N; 2.10 moles) is added to the reaction over 7 minutes during which time the temperature increases to 62° C. The reaction is heated to reflux (78° C.) and held for 1 hr. Water (1.96 L) is added to the reaction at once. The temperature decreases to 68° C. The reaction is heated back to reflux (79° C.) and a solution forms. Darco G-60® (438 g) is added to the reaction. The reaction is held at reflux for 1.25 hours. The hot Darco G-60® slurry is filtered through GFF paper into another 22 L flask. A light yellow solution results. The original flask and Darco G-60® filter cake are rinsed with hot ethanol (2.5 L). During the rinse, solid begins to form in the filtrate. The 22 L flask containing the filtrate and wash is equipped with overhead stirring, nitrogen inlet, and a thermocouple. The slurry is stirred and allowed to cool to ambient temperature. The solid is filtered and washed with ethanol (2 L). The wet cake weight is 672 g. The solid is dried in vacuo at 50° C. to give 540 g (68.9% yield) of 4-[5-(2-amino-ethanesulfonyl)-isoquinolin-7-yl]-phenol monohydrochloride hemihydrate. Mass Spectrum (LCMS) m/z=329.3) (M+H$^+$).

The exemplified compounds are inhibitors of Akt activity. The inhibitory activity of these compounds may be demonstrated by the methods below.

Akt1 Phosphorylation Assay

The assay measures the phosphorylation of PKC alpha pseudo-substrate peptide by a Competitive Fluorescence Polarization Immunoassay (FPIA). The assay indirectly measures the concentration of phospho-peptide product formed in a reaction by measuring the change in the intensity of polarized light emitted from a fluorescently-labeled tracer peptide when displaced from a phospho-specific antibody by the phospho-peptide product. Calibration with a standard curve yields quantitative results.
Enzyme and Substrate
Active human recombinant Akt1 (full-length) purified from Sf9 insect cells is obtained from Upstate Biotechnology, Inc. Peptide Substrate (M.W.1561) is purchased.
Standard Assay Solutions
Solution (A): 20% DMSO (dimethylsulphoxide) or Compound in 20% DMSO or 500 mM EDTA; Solution (B): Assay Buffer Mix: 75 µM Peptide Substrate, 38 mM $MgCl_2$, 70 mM HEPES, pH 7.4, 0.01% Triton X-100®, and 50 µM ATP (adenosine triphosphate); Solution (C): Akt Kinase Mix: 70 mM HEPES, pH 7.4, 1 mM DTT (dithiothreitol), 0.01% Triton-X-100®, and Akt1 enzyme.
Procedure for FPIA
Five µL of Solution (A) are first mixed with 10 µL Solution (B). The enzymatic reaction is initiated by adding 10 µL Solution (C) to the mixture. (Final concentration or amount in a 25 µL reaction mix: 4% DMSO (minimal inhibited wells) or various compound concentration in 4% DMSO or 100 mM EDTA (maximal inhibited wells); 30 µM Peptide Substrate; 15 mM $MgCl_2$; 70 mM HEPES, pH 7.4; 20 µM ATP; 0.4 mM DTT; 0.01% Triton X-100®). The reactions are performed in black half-area flat-bottom 96-well microtiter plates.
After 60 min at room temperature the reaction is terminated by adding 25 µL of Quench/Detection Mix containing 260 mM EDTA, 3.4 nM Fluorescein Tracer, and 7.5 nM Anti-Phosphoserine Antibody. The plates are incubated in darkness at room temperature for more than 3 hr, and then fluorescence polarization (at $\lambda_{ex}$=485 nm, $\lambda_{ex}$=530 nm) is read using a Tecan Ultra plate reader. The concentration of phosphorylated product per well is calculated from millipolarization (mP) units using a prepared peptide competitor dilution series as a standard curve. Exemplified compounds of the invention inhibit Akt1 phosphorylation with an $IC_{50}$ of 1 µM or less. The compound of Example 1 inhibits Akt1 phosphorylation in this assay with an $IC_{50}$ of 45+/−17 nM (n=3).

Cell-Based ELISA (cELISA) for the Detection of Phospho-GSK3b (pGSK3b)

A Target of Akt in Cells

Exponentially grown U87MG cells derived from a human glioblastoma are seeded into 96-well plates and incubated overnight at 37° C. with 5% $CO_2$. Ten concentrations of the compound of Example 1 are prepared from a 4 mM stock (in 100% DMSO) by 1:2 serial dilutions into the culture media. Equal volume of each of the serial dilutions is added directly to the cells. Treatment is stopped 2 hr later. At the end of the treatment, the culture media is removed, and the cells are washed once with ice-cold phosphate-buffered saline (PBS). The cells are fixed in PREFER according to vendor's procedure, followed by rinses in PBS/0.1% SDS and PBS/0.1% Triton X-100®, then overnight incubation in SEA Block Blocking buffer. The blocking step is followed by an overnight incubation of the cells with a rabbit antibody against pGSK3b/Ser9, followed by a goat anti-rabbit IgG. The pGSK3b is detected by SuperSignal ELISA Femto following the vendor's procedure. The compound of Example 1 inhibits pGSK3b in this assay with an $IC_{50}$ of 2.04+/−0.68 (n=8) µM.

In Vivo Target Inhibition Studies

In Vivo Target Inhibition by a Single IV Injection:
Exponentially growing U87MG cells derived from a human glioblastoma are implanted subcutaneously in the rear flank of nude mice. When the tumors reach the size of 200-250 $mm^3$, compounds are administered to the animals by a single IV injection in a dose-response study or in a time-course study. At the end of each treatment, animals are asphyxiated with $CO_2$. Tumors are harvested by surgical excision, quickly frozen in liquid nitrogen and stored at −80° C. until analysis. Sera are prepared from blood harvested from the heart by cardiac puncture and stored at −80° C. until analysis.
Sample Analysis:
The Akt inhibitor is extracted from serum with acetonitrite/methanol and analyzed alongside an internal standard by LC/MS/MS. Tumors are homogenized in 2 volumes of a lysis buffer containing 25 mM Tris (pH 7.5), Roche complete protease inhibitors, and 1 mM vanadate with Powergen 125 homogenizer, then sequentially passed thorough an 18 gauge needle and a 23 gauge needle. Soluble cytoplasmic extracts are collected from the supernatant fraction after the lysates are centrifuged for 30 minutes at 20,000×g. Protein concentrations in the cytoplasmic extracts are determined with a BCA kit. Phospho-GSK3b (pGSK3b) in the soluble extracts is analyzed with the ELISA Kit.
For glioblastoma in this assay, the compound of Example 1 inhibits pGSK3b by 76% at 1 hour using single IV injection of 25 mg/kg.

In Vivo Tumor Growth Inhibition Studies

Exponentially growing U87MG cells derived from a human glioblastoma or H1155 cells derived from human non-small cell lung cancer are implanted subcutaneously in the rear flank of nude mice. Three days after tumor cell implants, microsurgery is performed to cannulate catheter for continuous infusion via jugular vein. Example 1, formulated in D5W (5% dextrose in water) at various concentrations, is then infused into mice next day at 40 µL/hr for 4 days. Tumors are measured twice weekly until the study is terminated, usually at 24 days after the initial implants. Tumor growth inhibition is calculated by dividing the average tumor volume of the treated group by that of the vehicle-treated group.
For glioblastoma, the compound of Example 1 inhibits tumor growth by 50% using continuous infusion of 27 mg/kg/day when measured at the end of the assay.
For non-small cell lung cancer, the compound of Example 1 inhibits tumor growth by 63% using continuous infusion of 24 mg/kg/day when measured at the end of the assay.

Pharmaceutical Composition Studies

A pharmaceutical composition of 4-[5-(2-amino-ethane-sulfonyl)-isoquinolin-7-yl]-phenol monohydrochloride hemihydrate comprises a non-reducing sugar and a pH adjusting agent. Solubility studies show that mannitol does not appear to impact the solubility of 4-[5-(2-amino-ethane-sulfonyl)-isoquinolin-7-yl]-phenol monohydrochloride hemihydrate. However, the hemihydrate's solubility is pH dependent and is >19 mg/mL at pH≦3.91. Also, the rate at which precipitation takes place is pH dependent.

TABLE 1

Effect of initial solution pH on rate of precipitation (ppt).

| Media | pH (initial) | Precipitation (ppt) |
|---|---|---|
| 0.05 N HCl/3% mannitol | 1.68 | no ppt up to 96 hours |
| 0.01 N HCl/3% mannitol | 3.19 | no ppt up to 96 hours |
| 0.005 N HCl/3% mannitol | 3.58 | ppt after 48 hr |
| 0.0025 N HCl/3% mannitol | 3.91 | ppt after 36 hr |
| 0.001 N HCl/3% mannitol | 4.20 | ppt after 24 hr |

All solutions are prepared initially at approximately 15 mg 4-[5-(2-amino-ethanesulfonyl)-isoquinolin-7-yl]-phenol monohydrochloride hemihydrate/mL and stored at room temperature.

LC/MS analysis of the re-dissolved precipitate indicates that it is a "dimer-like" molecule (Mass spectrum (LCMS) m/z=640.2 (M+H$^+$)) that forms from two 4-[5-(2-Amino-ethanesulfonyl)-isoquinolin-7-yl]-phenol molecules (Mass spectrum (LCMS) m/z=329.1 (M+H$^+$) for 4-[5-(2-Amino-ethanesulfonyl)-isoquinolin-7-yl]-phenol) after the loss of ammonia. Additionally, precipitation does not appear to be due to a change to a less soluble solid state form.

We claim:

1. A compound which is 4-[5-(2-Amino-ethanesulfonyl)-isoquinolin-7-yl]-phenol or a pharmaceutically acceptable salt thereof, a hydrate of the compound, or a hydrate of a pharmaceutically acceptable salt of the compound.

2. The compound according to claim 1 which is 4-[5-(2-Amino-ethanesulfonyl)-isoquinolin-7-yl]-phenol di-hydrochloride.

3. The compound according to claim 1 which is 4-[5-(2-Amino-ethanesulfonyl)-isoquinolin-7-yl]-phenol monohydrochloride hemihydrate.

4. A method of treating multiple myeloma, non small cell lung cancer, glioblastoma, neuroblastoma, melanoma, or neoplasms of the prostate, breast, ovaries, primary stomach, intestinal-type, endometrium, thyroid, pancreas, lung, or bladder in a patient in need thereof comprising administering an effective amount of the compound or a pharmaceutically acceptable salt thereof, a hydrate of the compound, or a hydrate of a pharmaceutically acceptable salt of the compound of claim 1.

5. A method of treating multiple myeloma, non small cell lung cancer, glioblastoma, or neoplasms of the prostate, breast, or ovaries comprising in a patient in need thereof comprising administering an effective amount of the compound or a pharmaceutically acceptable salt thereof, a hydrate of the compound, or a hydrate of a pharmaceutically acceptable salt of the compound of claim 1.

6. A method of treating non small cell lung cancer or glioblastoma in a patient in need thereof comprising administering an effective amount of the compound or a pharmaceutically acceptable salt thereof, a hydrate of the compound, or a hydrate of a pharmaceutically acceptable salt of the compound of claim 1.

7. A method of treating hepatitis C, rubella, human immunodeficiency virus (HIV), hepatitis B, or human cytomegalovirus (HCMV) in a patient in need thereof comprising administering an effective amount of the compound or a pharmaceutically acceptable salt thereof, a hydrate of the compound, or a hydrate of a pharmaceutically acceptable salt of the compound of claim 1.

8. A pharmaceutical composition comprising the compound or a pharmaceutically acceptable salt thereof, a hydrate of the compound, or a hydrate of a pharmaceutically acceptable salt of the compound according to claim 1, and a pharmaceutically acceptable carrier, diluent or excipient.

9. A lyophilized pharmaceutical composition comprising the compound or a pharmaceutically acceptable salt thereof, a hydrate of the compound, or a hydrate of a pharmaceutically acceptable salt of the compound according to claim 1, and a pharmaceutically acceptable carrier, diluent or excipient wherein the pH of said composition when diluted with aqueous diluent is less than 4.2 and greater than 2.0.

10. The lyophilized pharmaceutical composition according to claim 9 wherein the pH of said composition when diluted with aqueous diluent is less than 3.2 and greater than 2.0.

11. The lyophilized pharmaceutical composition according to claim 10 wherein the pH of said composition when diluted with aqueous diluent is less than 2.8 and greater than 2.0.

12. A pharmaceutical composition comprising the compound or a pharmaceutically acceptable salt thereof, a hydrate of the compound, or a hydrate of a pharmaceutically acceptable salt of the compound according to claim 1, and a pharmaceutically acceptable carrier, diluent or excipient in solution wherein the pH of said composition is less than 4.2 and greater than 2.0.

13. The pharmaceutical composition according to claim 12 wherein the pH of said composition is less than 3.2 and greater than 2.0.

14. The pharmaceutical composition according to claim 13 wherein the pH of said composition is less than 2.8 and greater than 2.0.

15. 4-[5-(2-Amino-ethanesulfonyl)-isoquinolin-7-yl]-phenol monohydrochloride hemihydrate in crystalline form having an X-ray powder diffraction pattern with intense peaks at 2θ=4.9, 14.8, and 10.2.

16. The compound of claim 1 or a pharmaceutically acceptable salt thereof or a hydrate of a pharmaceutically acceptable salt of the compound.

* * * * *